(12) United States Patent
Alnabulsi et al.

(10) Patent No.: US 9,649,045 B2
(45) Date of Patent: May 16, 2017

(54) PNEUMATIC CIRCULATORY ENHANCER FOR DIABETIC LEG THERAPY

(71) Applicants: Baraa Alnabulsi, Chicago, IL (US); Alwaleed Al-Sawaf, Chicago, IL (US); Nazeeh Alothmany, Jeddah (SA); Nedim Turkmen, Jeddah (SA); Hamza Diken, Jeddah (SA); Abdulelah Aqeil, Munich (DE)

(72) Inventors: Baraa Alnabulsi, Chicago, IL (US); Alwaleed Al-Sawaf, Chicago, IL (US); Nazeeh Alothmany, Jeddah (SA); Nedim Turkmen, Jeddah (SA); Hamza Diken, Jeddah (SA); Abdulelah Aqeil, Munich (DE)

(*) Notice: Subject to any disclaimer, the term of this patent is extended or adjusted under 35 U.S.C. 154(b) by 933 days.

(21) Appl. No.: 14/011,343

(22) Filed: Aug. 27, 2013

(65) Prior Publication Data
US 2015/0065931 A1 Mar. 5, 2015

(51) Int. Cl.
*A61H 9/00* (2006.01)
*A61B 5/0452* (2006.01)
(Continued)

(52) U.S. Cl.
CPC ......... *A61B 5/0452* (2013.01); *A61H 9/0078* (2013.01); *A61B 5/0002* (2013.01);
(Continued)

(58) Field of Classification Search
CPC ... A61B 5/0452; A61B 5/0002; A61B 5/4836; A61B 5/0472; A61H 9/0078; A61H 2201/501; A61H 2201/5089; A61H 2209/00; A61H 2201/1246; A61H 2201/5071; A61H 2205/12; A61H 2201/5092; A61H 2201/5012; A61H 2201/1215; A61H 2033/143;
(Continued)

(56) References Cited

U.S. PATENT DOCUMENTS 5,458,562 A 10/1995 Cooper
6,468,237 B1 10/2002 Lina
(Continued)

FOREIGN PATENT DOCUMENTS

CN 102227190 10/2011
WO 2011/082176 7/2011

*Primary Examiner* — Quang D Thanh
(74) *Attorney, Agent, or Firm* — Oblon, McClelland, Maier & Neustadt, L.L.P.

(57) ABSTRACT

A pneumatic circulatory enhancer to enhance a blood flow of a leg of a patient that includes a chamber that surrounds the leg and is filled with gas having a negative, a zero-point, or a pressure, a pneumatic gas pump having a cylinder and a piston, the piston moving in the cylinder by an electrical motor, a plurality of ECG electrodes that are connected to body parts of the patient, a pressure sensor that is connected to the chamber and measures a pressure of the gas inside the chamber, a controller that receives the ECG signals from the plurality of ECG electrodes and controls the electrical motor based on the received ECG signals to pump-in or pump-out the gas from the chamber by moving the piston inside the chamber such that the zero-point pressure is an atmospheric pressure of a location that the pneumatic circulatory enhancer is operated.

18 Claims, 10 Drawing Sheets

(51) Int. Cl.
*A61B 5/0472* (2006.01)
*A61H 33/14* (2006.01)
*A61B 5/00* (2006.01)

(52) U.S. Cl.
CPC ........... *A61B 5/0472* (2013.01); *A61B 5/4836* (2013.01); *A61H 2033/143* (2013.01); *A61H 2201/1215* (2013.01); *A61H 2201/1246* (2013.01); *A61H 2201/501* (2013.01); *A61H 2201/5007* (2013.01); *A61H 2201/5012* (2013.01); *A61H 2201/5071* (2013.01); *A61H 2201/5089* (2013.01); *A61H 2201/5092* (2013.01); *A61H 2201/5097* (2013.01); *A61H 2205/06* (2013.01); *A61H 2205/082* (2013.01); *A61H 2205/106* (2013.01); *A61H 2205/12* (2013.01); *A61H 2209/00* (2013.01); *A61H 2230/065* (2013.01); *A61H 2230/305* (2013.01)

(58) Field of Classification Search
CPC ........ A61H 2201/5007; A61H 2205/06; A61H 2201/5097; A61H 2205/082; A61H 2230/305; A61H 2205/106; A61H 2230/065
See application file for complete search history.

(56) References Cited

U.S. PATENT DOCUMENTS

| | | | |
|---|---|---|---|
| 7,214,202 | B1 | 5/2007 | Vogel et al. |
| 8,235,921 | B2 | 8/2012 | Rousso et al. |
| 2005/0027218 | A1* | 2/2005 | Filtvedt ............... A61F 7/00 601/152 |
| 2008/0021531 | A1* | 1/2008 | Kane .................. A61F 7/02 607/111 |
| 2008/0208088 | A1* | 8/2008 | Cazzini ............ A61M 1/0088 602/13 |
| 2009/0270910 | A1 | 10/2009 | Hargens et al. |
| 2010/0210983 | A1 | 8/2010 | Baker et al. |
| 2012/0238924 | A1 | 9/2012 | Avni |

* cited by examiner

PNEUMATIC CIRCULATORY ENHANCER FOR DIABETIC LEG THERAPY

GRANT OF NON-EXCLUSIVE RIGHT

This application was prepared with financial support from the Saudi Arabian Cultural Mission (SACM), and in consideration therefore the present inventor has granted The Kingdom of Saudi Arabia a non-exclusive right to practice the present disclosure.

BACKGROUND

Field of the Disclosure

The present disclosure relates to a pneumatic circulatory enhancer for diabetic leg therapy, and more particularly, relates to a pneumatic circulatory enhancer for diabetic leg therapy that enhances the blood flow in a diabetic foot.

BRIEF SUMMARY

It is an object of the present disclosure to provide a pneumatic circulatory enhancer to enhance a blood flow of a leg of a patient. The pneumatic circulatory enhancer includes a chamber that surrounds the leg made of horizontal compartments with barriers in between consisting of holes to allow gas flow between compartments, the compartment is filled with gas having a negative pressure, a zero-point pressure, or a positive pressure; a pneumatic gas pump having a cylinder and a piston that is connected to the lower compartment of the chamber via a tube, the piston moving in the cylinder by an electrical motor; a plurality of ECG electrodes that are connected to body parts of the patient and detect ECG signals, which are indicators of heartbeats of the patient, from the patient; a pressure sensor that is connected to the chamber and measures a pressure of the gas inside the chamber; blood pressure sensor connected to the patient to measure the arterial blood pressure of the patient; a controller that receives the ECG signals from the plurality of ECG electrodes as well as the patient blood pressure signal and controls the electrical motor based on either the received ECG signals or the arterial blood pressure to pump-in/pump-out the gas to/from the chamber by moving the piston inside the chamber such that the zero-point pressure is an atmospheric pressure that the pneumatic circulatory enhancer is operated, the negative pressure is any pressure smaller than the zero-point pressure, and the positive pressure is any pressure greater than the zero-point pressure.

It is an object of the present disclosure to provide a pneumatic circulatory enhancer such that the controller via the pneumatic gas pump increases or decreases the pressure of the gas inside the chamber in-synchrony with the direction of blood flow coming out or into the heart of the patient.

It is an object of the present disclosure to provide a pneumatic circulatory enhancer such that upon determination by the controller, based on the received ECG signals, or the arterial blood pressure that the heart of the patient is pumping the blood into the leg, the controller moves the piston to generate the negative pressure inside the chamber, and upon determination by the controller, based on the received ECG signals or the arterial blood pressure, that the heart of the patient is pumping the blood out of the leg, the controller moves the piston to generate the positive pressure inside the chamber.

It is an object of the present disclosure to provide a pneumatic circulatory enhancer such that upon determination of a QRS-wave by the controller, based on the received ECG signals, or maximum pressure value in the arterial blood pressure waveform, the electrical motor moves the piston to decrease the pressure of the gas inside the chamber, and upon determination of a T-wave by the controller, based on the received ECG signals, or the minimum pressure value in the arterial blood pressure waveform, the electrical motor moves the piston to increase the pressure of the gas inside the chamber which is going to be filled one chamber at a time (bottom to top) to squeeze the leg and push the blood upwards towards the heart.

It is an object of the present disclosure to provide a pneumatic circulatory enhancer that includes a sealer that is positioned between the chamber and the leg in an opening of the chamber and seals the opening of the chamber to prevent air leak from the chamber; and a ventilation valve that is connected to the chamber and is controlled by the controller.

It is an object of the present disclosure to provide a pneumatic circulatory enhancer that includes an oxygen tank connected to the chamber via an oxygen valve, the oxygen valve being controlled by the controller, to supply oxygen to the chamber when the valve is open; and an oxygen sensor connected to the chamber that measures a concentration of the oxygen gas inside the chamber and transmits measured oxygen concentration to the controller.

It is an object of the present disclosure to provide a pneumatic circulatory enhancer such that the chamber has a first part and a second part, and the first part and the second part rotate around a plurality of hinges, and the leg is positioned in the first part, and the second part is rotated around the hinges to surround the leg between the first part and the second part.

It is an object of the present disclosure to provide a pneumatic circulatory enhancer such that the pressure of the gas inside the chamber corresponds to the wave form the ECG signal or the arterial blood pressure of the patient.

It is an object of the present disclosure to provide a method for enhancing blood flow in a leg of a patient, that includes the steps of placing the leg inside a chamber and sealing an opening of the chamber to prevent air leak from the chamber; monitoring the patients heartbeats via a plurality of ECG electrodes that are connected to the patient; detecting, by a controller, a wave shape of ECG signals received from the ECG electrodes connected to the patient; monitoring the arterial blood pressure of the patient by a blood pressure sensor that is connected to the patient and feeds the blood pressure to the controller; monitoring the pressure of the gas inside the chamber; and adjusting the pressure inside the chamber based on the wave shape of the ECG signals or blood pressure waveform such that when the controller detects, based on the received ECG signals, or the blood pressure waveform that the heart of the patient is pumping the blood into the leg, the pressure of the chamber is decreased, and when the controller detects, based on the received ECG signals, or the blood pressure waveform that the heart of the patient is pumping the blood out of the leg, the pressure of the chamber is increased.

It is an object of the present disclosure to provide a method for enhancing blood flow in a leg of a patient such that the pressure of the chamber is decreased to increase the delivery of blood from heart to the leg, and the pressure of the chamber is increased to the push the blood from the leg back to the heart.

It is an object of the present disclosure to provide a method for enhancing blood flow in a leg of a patient such that the pressure of the gas inside the chamber is adjusted in-synchrony with the direction of blood flow out or into the heart of the patient.

It is an object of the present disclosure to provide a method for enhancing blood flow in a leg of a patient that includes the steps of decreasing the pressure of the gas inside the chamber when a QRS-wave is detected in the received ECG signals; or a maximum is detected in the blood pressure waveform; and increasing the pressure of the gas inside the chamber when a T-wave is detected in the received ECG signals or a minimum is detected in the blood pressure waveform.

It is an object of the present disclosure to provide a method for enhancing blood flow in a leg of a patient that includes the steps of opening a ventilation valve for pumping out the gas in chamber; opening an oxygen valve for filling the chamber with oxygen from an oxygen tank; monitoring a concentration of the oxygen inside the chamber; and closing the oxygen valve and the ventilation valve when the concentration of the oxygen gas inside the chamber is above a predetermined threshold.

It is an object of the present disclosure to provide a method for enhancing blood flow in a leg of a patient that includes the steps of measuring the pressure of the gas after the step of adjusting; determining whether or not the measured pressure of the gas inside the chamber is outside of a predetermined pressure range; adjusting the pressure of the gas to zero-point pressure and obtaining a next ECG signal or blood pressure signal from the patient body when the measured pressure of the gas is outside the predetermined pressure range; and obtaining a next ECG signal or blood pressure signal from the patient body when the measured pressure of the gas in within the predetermined range.

It is an object of the present disclosure to provide a non-transitory computer readable medium including executable instructions, which when executed by a controller, cause the processor execute a method for enhancing blood flow in a leg of a patient, the method includes the steps of monitoring the patients heartbeats via a plurality of ECG electrodes that are connected to the patient; detecting a wave shape of ECG signals received from the ECG dectrodes connected to the patient; monitoring the arterial blood pressure of the patient, detecting the wave shape of the blood pressure waveform; monitoring the pressure of the gas inside a chamber surrounding the leg of the patient via a pressure sensor connected to the chamber; and adjusting the pressure inside the chamber based on the wave shape of the ECG signals or blood pressure waveform by moving a piston of an air pump with an electrical motor such that when the controller detects, based on the received ECG signals, or the blood pressure waveform that the heart of the patient is pumping the blood into the leg, the pressure of the chamber is decreased, and when the controller detects, based on the received ECG signals, or the blood pressure waveforms that the heart of the patient is pumping the blood out of the leg, the pressure of the chamber is increased.

It is an object of the present disclosure to provide the non-transitory computer readable medium that performs the steps of decreasing the pressure of the gas inside the chamber when a QRS-wave; or a maximum value in blood pressure waveform is detected and increasing the pressure of the gas inside the chamber when a T-wave or a minimum in the blood pressure waveform is detected.

It is an object of the present disclosure that when a QRS-wave or maximum in blood pressure is detected that the gas is filled inside the chamber one compartment at a time resulting in pressure increase from the bottom upwards to ensure that the blood flows upwards towards the heart It is an object of the present disclosure to provide the non-transitory computer readable medium that performs the steps of opening a ventilation valve for pumping out the gas in chamber; opening an oxygen valve for filling the chamber with oxygen from an oxygen tank; monitoring a concentration of the oxygen inside the chamber; and closing the oxygen valve and the ventilation valve when the concentration of the oxygen gas inside the chamber is above a predetermined threshold.

It is an object of the present disclosure to provide the non-transitory computer readable medium, that performs a method that includes the steps of measuring the pressure of the gas after the step of adjusting; determining if the measured pressure of the gas inside the chamber is outside of a predetermined pressure range; adjusting the pressure of the gas when the measured pressure of the gas is outside the predetermined pressure range; and obtaining a next ECG signal or blood pressure waveform from the patient body when the measured pressure of the gas in within the predetermined range.

DETAILED DESCRIPTION

Figure 1:
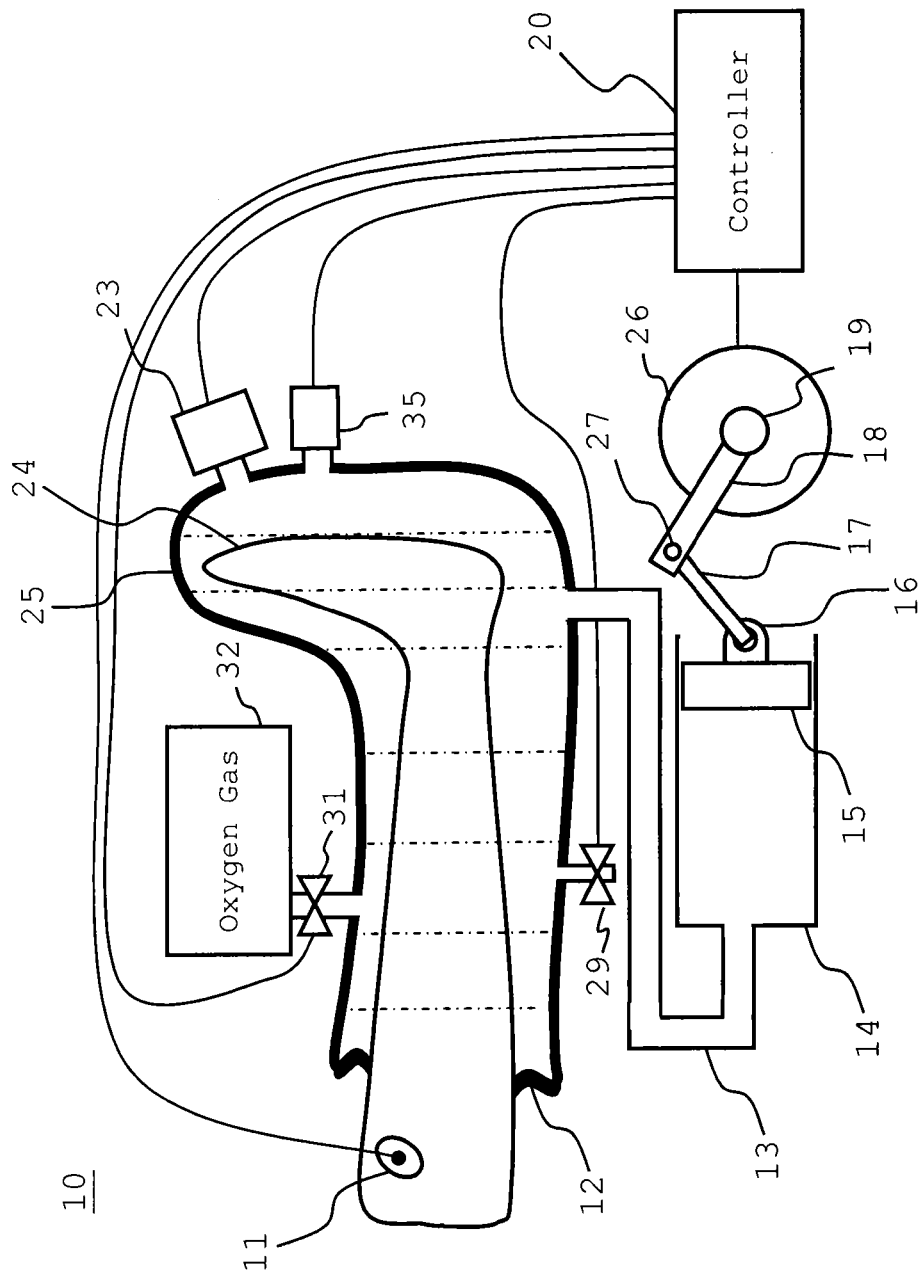
FIG. 1 is an exemplary embodiment of a pneumatic circulatory enhancer for diabetic leg therapy.

FIG. 1 illustrates an exemplary embodiment of a pneumatic circulatory enhancer 10 for diabetic leg therapy. The pneumatic circulatory enhancer 10 includes a chamber 25 around an affected foot 24. The affected foot 24 can be inserted into and/or placed in the chamber 25. The chamber 25 may be in any shape to surround the affected foot 24. For example, the chamber 25 may have a boot shape, a cube, or a tube that is made of, for example, rigid and, optionally, transparent materials. Examples of the rigid and transparent materials include, but are not limited to, glass, thermoplastics such as acrylic (Poly(methyl methacrylate)), and polyvinyl chloride. The chamber 25 may be made of non-transparent or semi-transparent materials. The chamber 25 may surround any portion of the affected foot 24. For example, the chamber 25 may surround the affected foot 24 above the knee, below the knee, or up to the mid-thigh. The chamber 25 is made of compartments running horizontally with holes in between to allow gas to move between compartments.

A sealer 12 seals the affected foot 24 in the chamber 25 in an opening of the chamber 25 where the affected foot is inserted into the chamber 25. The sealer 12 seals the affected foot 24 in the chamber 25 in order to reduce and/or prevent air leakage. The sealer 12 may be, for example, a rubber sealing grommet or a shrink-to-fit rubber sealing grommet. The sealer 12 may be, for example, disposable or non-disposable. Liquid, semi-liquid, and/or gel sealants may be used with the sealer 12 to further seal the affected foot in the chamber 25. Examples of sealants include, but are not limited to, medical grade adhesives, medical grade sealants, and medical grade oils.

Figure 2:
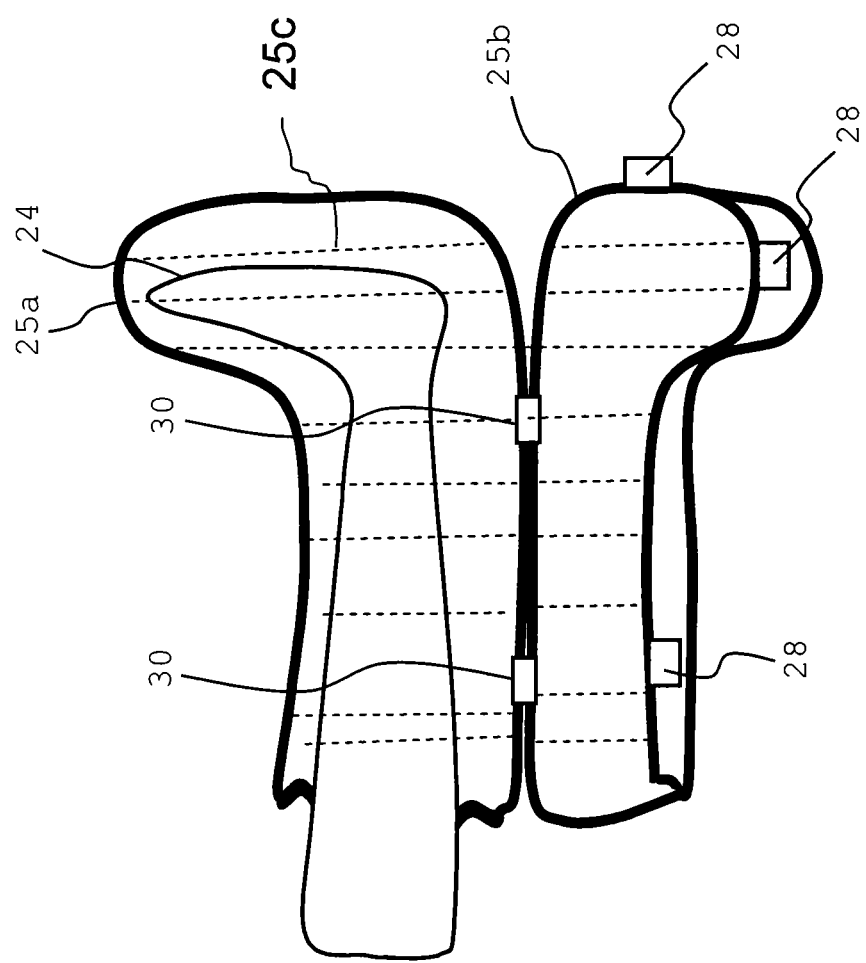
FIG. 2 is an exemplary embodiment of a chamber for a pneumatic circulatory enhancer for diabetic leg therapy.

In an exemplary embodiment of the present application, the chamber 25 may be a boot-shaped solid container that the affected foot 24 is inserted into as illustrated in FIG. 1. However, as shown in FIG. 2, which is another exemplary embodiment, a similar chamber having two or more separate parts 25a and 25b can be used such that the separate parts 25a and 25b are connected to each other with a plurality of hinges 30 as the chamber 25. In the case of the chamber 25 having two or more separate parts 25a and 25b (as shown in FIG. 2), the affected foot 24 is placed in the chamber when the chamber is open. Then, the separate parts 25a and 25b are flipped around the hinges 30 to be closed, sealed, and/or locked using a plurality of locks 28 to surround the affected foot 24. This exemplary embodiment provides an advantage that the affected foot 24 can be placed in the chamber for treatment with minimal disturbance to the affected foot 24. For simplicity of illustration, auxiliary components surrounding the chamber (as illustrated in FIG. 1) are not illustrated in FIG. 2. However, all of the components of FIG. 1 may be incorporated and used into the chamber as illustrated in FIG. 2 as well.

In a preferable embodiment the chamber contains compartments with holes to allow air to leak between compartments. He chamber may thus have a series or horizontally space separators and/or membranes which permit the movement of gas and/or pressure between horizontal sections of the chamber. The horizontally spaced separators are identified as feature 25c in FIG. 2. Similarly spaced separators may likewise be present in the chamber depicted in FIG. 1.

The chamber has an opening at the bottom to allow the cylinder to push the gas into it. FIG. 1 shows the opening at a position that is not at the most lower part of the chamber. In other embodiments the opening may be positioned at a toe or heel position of the chamber or otherwise at a lowermost portion of the chamber. When a lower chamber is filled with gas and the gas subsequently leaks between chambers one at a time to build the pressure in the leg gradually from the bottom to the top. In an embodiment of the invention the chambers are subject to sequential pressurization/depressurization to thereby provide a massaging or upward force from the foot toward the leg. The resultant squeezing effect on the foot bottom to top to push the blood outwards away from the foot towards the heart. Squeezing the leg without the sense of direction may result in blood flowing in a random pattern causing it to remain in the foot rather than exiting towards the heart.

Now returning to FIG. 1, the chamber 25 is connected to an air cylinder 14 via a tube 13 that connects the chamber 25 to the air cylinder 14. The tube 13 is located at the bottom of the chamber so that the gas pressure builds up starting from the lower compartment going upwards. The air cylinder 14 contains a piston 15 that when moved, can pump the air in and out of the air cylinder 14. The air cylinder 14 and the piston 15, collectively, are also referred to as the air pump in the present application. A first lever 17 is connected to the piston 15 via a piston pin boss 16. A pin 27 connects the first lever 17 to a second lever 18 such that the first lever 17 and the second lever 18 can freely rotate around the pin 27. The second lever 18 is connected to a rotating shaft 19 of a servo motor 26. A rotation of the rotating shaft 19 of the servo motor 26 causes the piston 15 to move forward and backward inside the air cylinder 14. Therefore, a rotation of the rotating shaft 19 of the servo motor 26 pumps in and/or out the air inside the air cylinder 14. It should be noted that the air pump, as disclosed in the present application, may be replaced by any similar air pump having similar functionality to pump and suck the air into and from the chamber 25, respectively. Such air pumps may have similar and/or different mechanism of operation and the functionality of the pneumatic circulatory enhancer 10 is independent of a type of air pump used to pump and suck the air in and out of the chamber 25.

The air cylinder 14 that is connected to the chamber 25 can increase or decrease the pressure inside the chamber 25 above and below atmospheric pressures. For example, when the air is pumped into the chamber 25, the pressure inside the chamber 25 is increased starting from the bottom compartment going upwards to the upper most compartment and when the pressure is pumped out of the chamber 25, the pressure inside the chamber 25 is decreased. A variation of the pressure inside the chamber may follow any arbitrary waveform. For example, FIGS. 7-10 illustrate examples of pressure variation inside the chamber 25. The inventors of the current application note that when the pressure of the inside the chamber follows the heartbeats of the patient, the blood flow into the affected foot is increased as the increased blood flow into the affected foot is advantageous for the diabetic patient in the therapy process as it is disclosed in this application.

In other words, the pneumatic circulatory enhancer 10 may pump and suck air in the chamber 25 in synchrony, for example, with the physiological heart function. When the heart contracts pumping the blood to the whole body, the pneumatic circulatory enhancer 10 sucks air from the chamber 25, creating a negative pressure inside the chamber 25, in which the leg 24 is placed. Reducing the pressure inside the chamber 25 while the heart contracts enhances the amount of blood rich in oxygen, nutrition, macrophages and even medications to reach the distal parts of the leg. Consequently, when the heart relaxes the pneumatic circulatory enhancer 10 pumps air inside the chamber 25, creating positive pressure inside the chamber 25, squeezing the leg 24 to support the venous return to the heart, evacuating the extravagating fluids into the interstitial space, and clearing the harmful metabolites. It should be noted that although the pneumatic circulatory enhancer 10, as disclosed in this application, is described to function in synchrony with heart beats, other embodiments, for example, manually overriding the pressure change in the chamber 25 or air pressure synchrony with any similar signal is also in the scope of this application.

The negative pressure and the positive pressure, as disclosed in this application, indicates any pressure below and above the base chamber 25 pressure, for example, the atmospheric pressure, respectively. Zero pressure or zero point pressure is defined as the base pressure, for example, the atmospheric pressure.

The waveform and/or the rate of the pressure increase and pressure decrease during the pumping in and sucking out the air from the chamber 25 can be, for example, linear, sine wave, square wave, triangle wave, saw-tooth wave, modulated pulse, exponential, or any combinations of them. Additionally, for each patient, a different pressure waveform may be used.

It is noted that the air inside the chamber 25 may be saturated with oxygen, thus providing the advantages of the Topical Hyperbaric Oxygen Therapy. The air inside the chamber 25 may be saturated with any other gas having therapeutic/sterilizing advantages. The pneumatic circulatory enhancer 10 can be controlled by the controller 20 that controls and adjusts the air pump to the heart beat through, for example, detecting the QRS complexes by using the ECG electrodes 11. Or detecting the maximum value for the blood pressure waveform by using BP electrode 11b The pneumatic circulatory enhancer 10 can be controlled by the controller 20, for example, to ensure that the process of supporting the normal function of the heart (i.e. contractions and relaxations) is not reversed. The pumping volume, pumping speed, pumping flow, and pumping pressure may be adjusted by, for example, adjusting the first lever 17, the second lever 18, air cylinder volume 14, piston 15, air cylinder cross sectional area, and the servo motor 26 characteristics.

One or more ECG electrodes 11 can send ECG signals from human body to the controller 20 to monitor the patient heart beats. The one or more ECG electrodes 11 or blood pressure sensor 11b may be connected to the controller 20 directly or via an amplifier (not shown) to amplify the ECG signals or BP waveforms from the patient. When the heart starts pumping blood into the circulation system inside human body, the controller 20 detects the R-wave (i.e. contraction of the heart & pumping blood to tissues) from the electrocardiogram (ECG) of the patient or the maximum pressure in the blood pressure waveform. When the R-wave is detected, or the maximum pressure is detected, the controller 20 actuates the servo motor 26 to suck the air from the chamber 25 surrounding the foot 24. When the air is sucked from the chamber 25 into the air cylinder 14, because the chamber is sealed, the pressure is reduced inside the chamber 25. Such a pressure increase, right after R-Wave, can increase the blood flow into the affected foot 24. Additionally, when the heart starts filling blood, the T-wave (i.e. relaxation of the heart returning of blood from tissues back to the heart) from the ECG, which are connected to the patient, is detected or the minimum blood pressure coming from the blood pressure sensor is detected and used as a control signal for the servo motor 26 to push more air into the chamber 25 around the affected foot 24. Pumping more air into the chamber 25 results in an increase in the pressure inside the chamber 25, which consequently increases the blood return from the affected foot 24 to the heart.

The chamber 25 further includes a ventilation valve 29 that is connected to a controller 20 via a cable. The ventilation valve 29 can be opened and closed by the controller 20. The ventilation valve 29 may be, for example, an electro-pneumatic control valves or similar valves that can be controlled electronically.

An oxygen gas tank 32 is connected to the chamber 25 via an oxygen valve 31. The oxygen valve 31 can be controlled by the controller 20. When the oxygen valve 31 is open, the oxygen flows into the chamber 25 from the oxygen tank 32. It is noted that the oxygen valve 31 can be controlled by the controller 20 to be partially open such that a flow of the oxygen from the oxygen tank 32 into the chamber 25 can be adjusted.

One or more oxygen sensors 35 are connected to the chamber 25 to monitor a concentration of oxygen inside the chamber 25. It is noted that additional gas sensors, for example, a nitrogen or carbon dioxide gas sensor may also be positioned on the chamber 25 to monitor a concentration of the corresponding gases. The gas sensors 35 may be universal gas sensors that can detect more than one gas. Examples of gas sensors include, but are not limited to, capacitive-type gas sensors, infra-red IR gas sensor, and/or laser-based gas detectors.

One or more pressure sensor 23 are connected to the chamber 25 to monitor the pressure inside the chamber 25. The pressure sensors 23 can send pressure reading to the controller 23 for processing and adjusting the pressure inside the chamber 25. Examples of pressure sensors include, but are not limited to, digital capacitance diaphragm gauges, and/or analogue capacitance diaphragm gauges. It is noted that the pressure sensors 23 precisely monitors the pressure around the zero point pressure.

Figure 3:
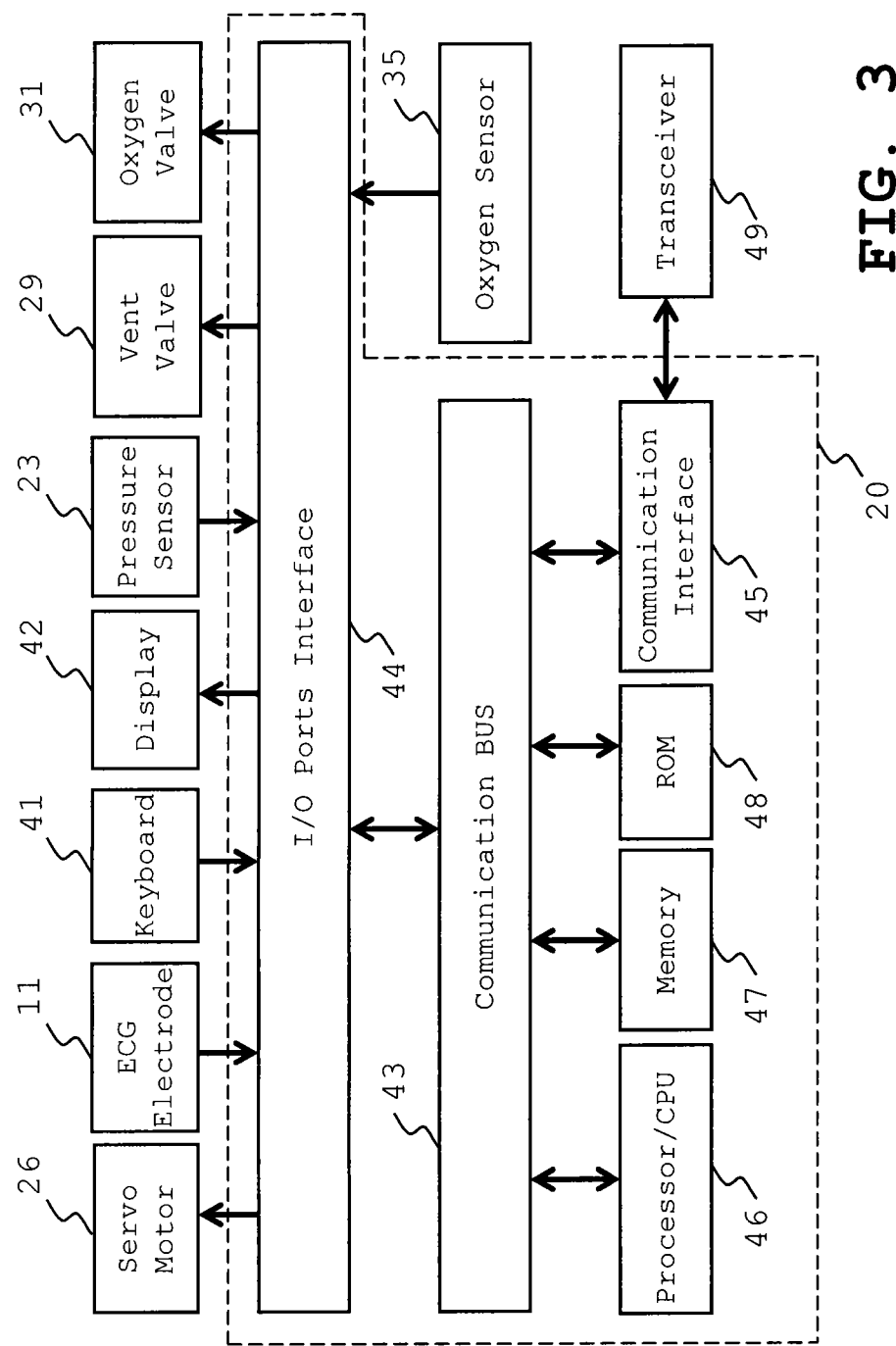
FIG. 3 is an exemplary block diagram of a controller that controls a pneumatic circulatory enhancer for diabetic leg therapy.

FIG. 3 is an exemplary block diagram of the controller 20 that controls the pneumatic circulatory enhancer 10 for diabetic leg therapy. The controller 20 includes a communication bus 43 or other communication mechanism for communicating information, and a CPU/processor 46 coupled with the communication bus 43 for processing the information. The controller 20 also includes a main memory 47, such as a random access memory (RAM) or other dynamic storage device (e.g., dynamic RAM (DRAM), static RAM (SRAM), and synchronous DRAM (SDRAM)), coupled to the communication bus 43 for storing information and instructions to be executed by processor 46. In addition, the main memory 47 may be used for storing temporary variables or other intermediate information during the execution of instructions by the processor 46. The controller 20 further includes a read only memory (ROM) 48 or other static storage device (e.g., programmable ROM (PROM), erasable PROM (EPROM), and electrically erasable PROM (EEPROM)) coupled to the communication bus 43 for storing static information and instructions for the processor 46.

The controller 20 may also include a disk controller (not shown) coupled to the communication bus 43 to control one or more storage devices for storing information and instructions, such as a magnetic hard disk, and a removable media drive (e.g., floppy disk drive, read-only compact disc drive, read/write compact disc drive, compact disc jukebox, tape drive, and removable magneto-optical drive). The storage devices may be added to the controller 20 using an appropriate device interface (e.g., small computer system interface (SCSI), integrated device electronics (IDE), enhanced-IDE (E-IDE), direct memory access (DMA), or ultra-DMA).

The controller 20 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The controller 20 may also include a display controller (not shown) coupled to the communication bus 43 to control a display 42, such as a cathode ray tube (CRT), for displaying information to a computer user. The controller 20 is connected to input devices, such as a keyboard 41 and/or a pointing device (not shown), for interacting with a computer user and providing information to the processor 46. The pointing device, for example, may be a mouse, a trackball, or a pointing stick for communicating direction information and command selections to the processor 46 and for controlling cursor movement on the display 42. In addition, a printer (not shown) may provide printed listings of data stored and/or generated by the controller 20.

The controller 20 performs a portion or all of the processing steps of the pneumatic circulatory enhancer 10 in response to the processor 46 executing one or more sequences of one or more instructions contained in a memory, such as the main memory 47. Such instructions may be read into the main memory 47 from another computer readable medium, such as a hard disk or a removable media drive. One or more processors in a multi-processing arrangement may also be employed to execute the sequences of instructions contained in main memory 47. In alternative embodiments, hard-wired circuitry may be used in place of or in combination with software instructions. Thus, embodiments are not limited to any specific combination of hardware circuitry and software.

As stated above, the controller 20 includes at least one computer readable medium or memory for holding instructions programmed according to the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present disclosure includes software for controlling the controller 20, for driving the pneumatic circulatory enhancer 10, and for enabling the controller 20 to interact with a human user (e.g., personnel operating the pneumatic circulatory enhancer 10). Such software may include, but is not limited to, device drivers, operating systems, development tools, and applications software. Such computer readable media further includes the computer program product of the present disclosure for performing all or a portion (if processing is distributed) of the processing performed in implementing the disclosure.

The computer code devices of the present disclosure may be any interpretable or executable code mechanism, including but not limited to scripts, interpretable programs, dynamic link libraries (DLLs), Java classes, and complete executable programs. Moreover, parts of the processing of the present disclosure may be distributed for better performance, reliability, and/or cost.

The term "computer readable medium" as used herein refers to any medium that participates in providing instructions to the processor 46 for execution. A computer readable medium may take many forms, including but not limited to, non-volatile media, volatile media, and transmission media. Non-volatile media includes, for example, optical, magnetic disks, and magneto-optical disks, such as the hard disk or the removable media drive. Volatile media includes dynamic memory, such as the memory 47. Transmission media includes coaxial cables, copper wire and fiber optics, including the wires that make up the communication bus 43. Transmission media also may also take the form of acoustic or light waves, such as those generated during radio wave and infrared data communications.

Various forms of computer readable media may be involved in carrying out one or more sequences of one or more instructions to processor 46 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the controller 20 may receive the data on the telephone line and use an infrared transmitter to convert the data to an infrared signal. An infrared detector coupled to the communication bus 43 can receive the data carried in the infrared signal and place the data on the bus 43. The communication bus 43 carries the data to the main memory 47, from which the processor 46 retrieves and executes the instructions. The instructions received by the main memory 47 may optionally be stored on storage device either before or after execution by processor 46.

The controller 20 also includes a communication interface 45 coupled to the communication bus 43. The communication interface 45 provides a two-way data communication coupling to a network link (not shown) that is connected to, for example, a local area network (LAN), or to another communications network such as the Internet. For example, the communication interface 45 may be a network interface card to attach to any packet switched LAN. As another example, the communication interface 45 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 45 sends and receives electrical, electromagnetic or optical signals that carry digital data streams representing various types of information. The communication interface may be further connected to a transceiver 49 that is further connected to the pneumatic circulatory enhancer 10.

The network link typically provides data communication through one or more networks to other data devices. For example, the network link may provide a connection to another computer through a local network (e.g., a LAN) or through equipment operated by a service provider, which provides communication services through a communications network. The local network and the communications network use, for example, electrical, electromagnetic, or optical signals that carry digital data streams, and the associated physical layer (e.g., CAT 5 cable, coaxial cable, optical fiber, etc). The signals through the various networks and the signals on the network link and through the communication interface 45, which carry the digital data to and from the controller 20 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The controller 20 can transmit and receive data, including program code, through the network(s), the network link and the communication interface 45. Moreover, the network link may provide a connection through a LAN to a mobile device (not shown) such as a personal digital assistant (PDA) laptop computer, or cellular telephone.

Further, the I/O ports interface 44 of the controller 20 is connected to the one or more ECG electrodes 11, the servo motor 26, the one or more pressure sensors 23, the vent valve 29, the oxygen valve 31, and the oxygen sensor 35. The I/O ports interface 44 sends and receive information from and to the one or more ECG electrodes 11, the servo motor 26, the one or more pressure sensors 23, the vent valve 29, the oxygen valve 31, and the oxygen sensor 35 in order to operate and control the pneumatic circulatory enhancer 10 for diabetic leg therapy.

Figure 4:
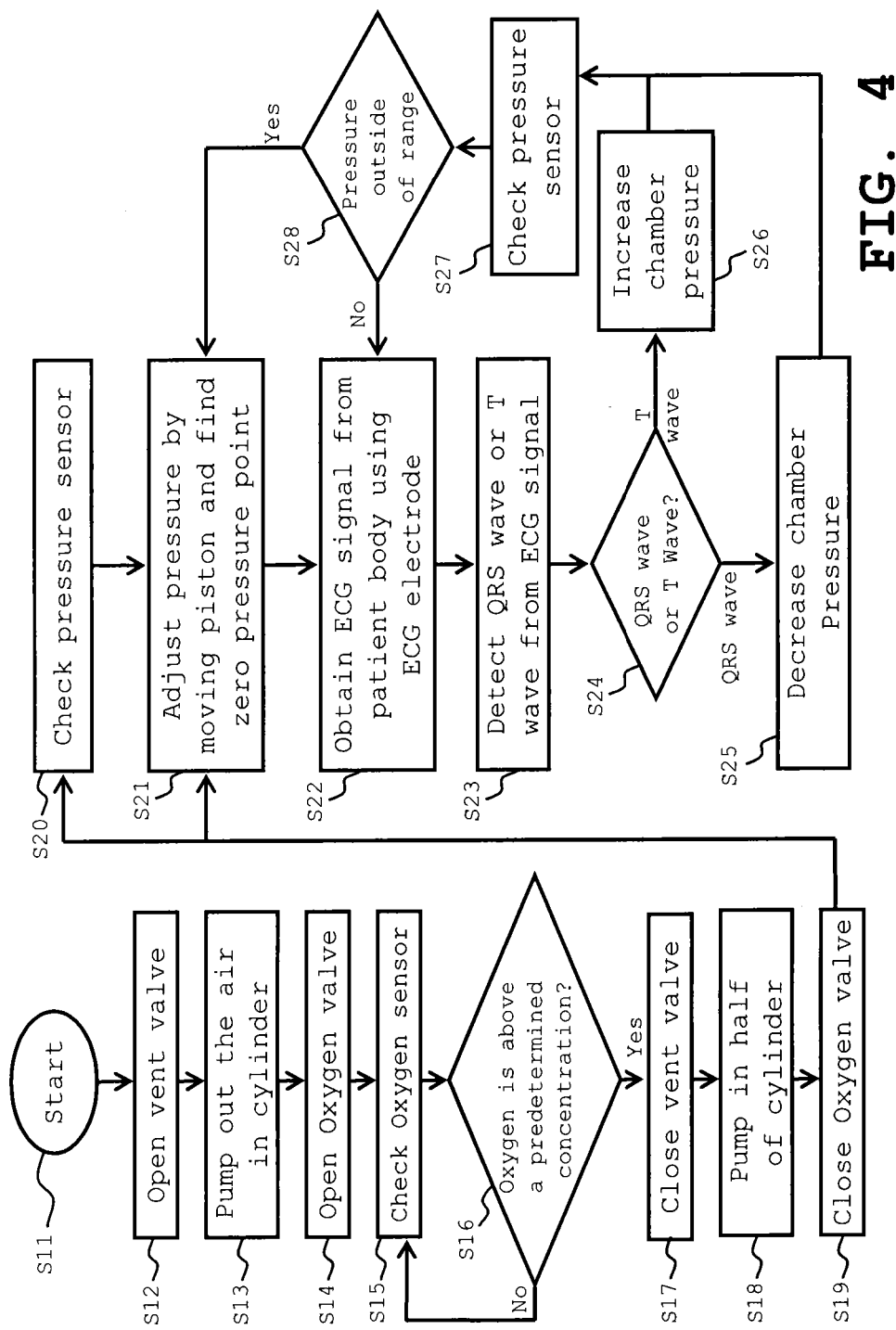
FIG. 4 is an exemplary flow chart of a method to operate a pneumatic circulatory enhancer for diabetic leg therapy.

FIG. 4 is an exemplary flow chart of a method to operate the pneumatic circulatory enhancer 10 for diabetic leg therapy.

At S11, the process starts. At this step, all of the parameters for operating the pneumatic circulatory enhancer 10 may be reset and the controller 20 and the pneumatic circulatory enhancer 10 may be initialized for operation. At this step, the initialization of the pneumatic circulatory enhancer 10 happens. The patient name and information may be entered into the controller 20 via the keyboard 41.

At S12, the vent valve 29 is opened. When the vent valve 29 is opened, the air can flow in and out of the chamber 25 to the ambient atmosphere.

At S13, the piston 15 pushes all of the air inside the air cylinder 14 into the chamber 25. In other words, the piston 15, evacuates the air cylinder 14 from any remnant gases inside the air cylinder 14. As illustrated in the FIG. 1, the piston 15 moves towards an end of the air cylinder 14 where the tube 13 is connected to the air cylinder 14.

At S14, the controller 20 opens the oxygen valve 31. The S14 is optional and may only be performed when the Topical Hyperbaric Oxygen Therapy is used. When the oxygen valve 31 is opened, the controller 20 waits for a predetermined period of time and/or for a predetermined oxygen concentration so that the oxygen can be filled up in the chamber 20. Filling the oxygen inside the chamber 25 flushes out any remnant gas inside the chamber 25 from the vent valve 29.

At S15, the oxygen sensor 35 check a concentration of the oxygen gas inside the chamber 25 and sends the oxygen concentration reading to the controller 20.

At S16, the controller determines whether or not the concentration of the oxygen inside the chamber 20 is above or below a predetermined threshold. For example, the predetermined threshold for the Topical Hyperbaric Oxygen Therapy may be set in advance by a medical professional or the factory in which the pneumatic circulatory enhancer 10 was fabricated. If the concentration of the oxygen inside the chamber 20 is below the predetermined threshold, the oxygen valve 31 is kept open so that more oxygen gas can flow into the chamber 25. If the concentration of the oxygen inside the chamber 20 is above the predetermined threshold, the process moves to S17, where the vent valve 29 is closed. The oxygen gas 32 may be supplied from any oxygen source, for example, from a commercial medical grade oxygen gas tank.

At S18, the piston 15 moves inside the air cylinder 14 to suck-in oxygen gas from the chamber 25 inside the air cylinder 14. Preferably, the movement of the piston 15 inside the air cylinder 14 fills substantially half of the air cylinder 14. It is noted that movement of the piston to empty the air cylinder 14 at S13 and the movement of the piston at S18 to fill half of the air cylinder at S18 are intended to flush the air cylinder 14 with oxygen. Positioning the piston 15 in the middle of the air cylinder 14 (where substantially half of the air cylinder 14 is filled) provides an advantage that the piston 15 can be adjusted to both negative pressure and positive pressure symmetrically.

At S19, the oxygen valve 31 is closed.

At S20, the pressure sensor 23 checks the pressure inside the chamber 25.

At S21, the piston 15 is moved inside the air cylinder 14 to adjust the pressure inside the chamber 25 while monitoring the pressure inside the chamber 25. The pressure is preferably set to a zero pressure point, which is, for example, the standard atmospheric pressure (1 ATM). Preferably, the zero point pressure is a pressure of a room in which the pneumatic circulatory enhancer 10 is placed and operated. However, the zero pressure point can be any predetermined pressure. When the pressure inside the chamber 25 is adjusted to be in the zero point pressure, the pneumatic circulatory enhancer 10 is ready for treating the leg 24 by synchronizing the pressure to the heart beats of the patient.

At S22, the ECG signals are obtained form the patient. One or more ECG electrodes 11 can be connected to different body parts of the patient to acquire the ECG signals.

At S23, the controller 20 detects QRS wave and/or T wave of the ECG signal as described in this application.

At S24, the controller 20 determines whether the QRS wave or a T wave is detected. If the controller determines that the QRS wave is detected, the process continues at step S25. If the controller determines that a T wave is detected, the process continues at step S26.

At S25, when the controller 20 detects that the QRS wave is detected, the controller 20 decreases the pressure inside the chamber 25 by actuating the servo motor 26. That is, the servo motor 26 in response to being actuated by the controller 20, moves the piston 15 such that the air inside the chamber 25 is sucked into the air cylinder 14. The pattern of movement of the servo motor 26 may be stored in advance in the memory 47. The movement of the servo motor 26 controls the pressure inside the chamber 25.

At S26, when the controller 20 detects that the T wave is detected, the controller 20 increases the pressure inside the chamber 25 by actuating the servo motor 26. That is, the servo motor 26, in response to being actuated by the controller 20, moves the piston 15 such that the air inside the chamber 25 is pumped into the air cylinder 14. The pattern of movement of the servo motor 26 may be stored in advance in the memory 47.

After both S25 and S26, the pressure inside the chamber is monitored at S27 by the pressure sensor 23. The pressure sensor 23 provides a feed back to the controller 20 about the pressure in the chamber 25 after the pressure is adjusted. Additionally, the patient may also provide feedback as to whether or not the applied negative and positive pressures, at their peak values, are tolerable by the patient. For example, if the patient indicates that a positive or a negative pressure is painful for the patient, based on this feed back, the operator may set a limit for the positive and negative pressure based on the feedback from the patient. In this case, the pressure would stay within the limits set by the operator.

At S28, the controller 20 compares the reading of the pressure sensor 23 at S27 with a preset reduced pressure value and a preset increased pressure value for the steps S25 and S26, respectively. Accordingly, the controller 20 determines whether or not the change in the pressure in response the QRS wave or T wave make the chamber pressure fall outside of a predetermined range for pressure. The controller 20 may adjust the pressure, at S21, by actuating the servo motor 26. The calibration results may be stored in the memory 47 of the controller 20. It should be noted that the controller 20 may repeat the steps S22 to S28 a number of time for calibration purposes. However, if the controller 20 at S28 determines that the change in the pressure in response the QRS wave or T wave is outside of a predetermined range for pressure, the controller 20 obtain the next sequence of the ECG signal at S22 and continues operation as discussed before. For secure operation, when the controller 20 determines that the pressure inside the chamber is outside of a predetermined range for pressure, the controller may open the vent valve 29 to prevent any damage to the foot 24 inside the chamber 25.

Figure 5:
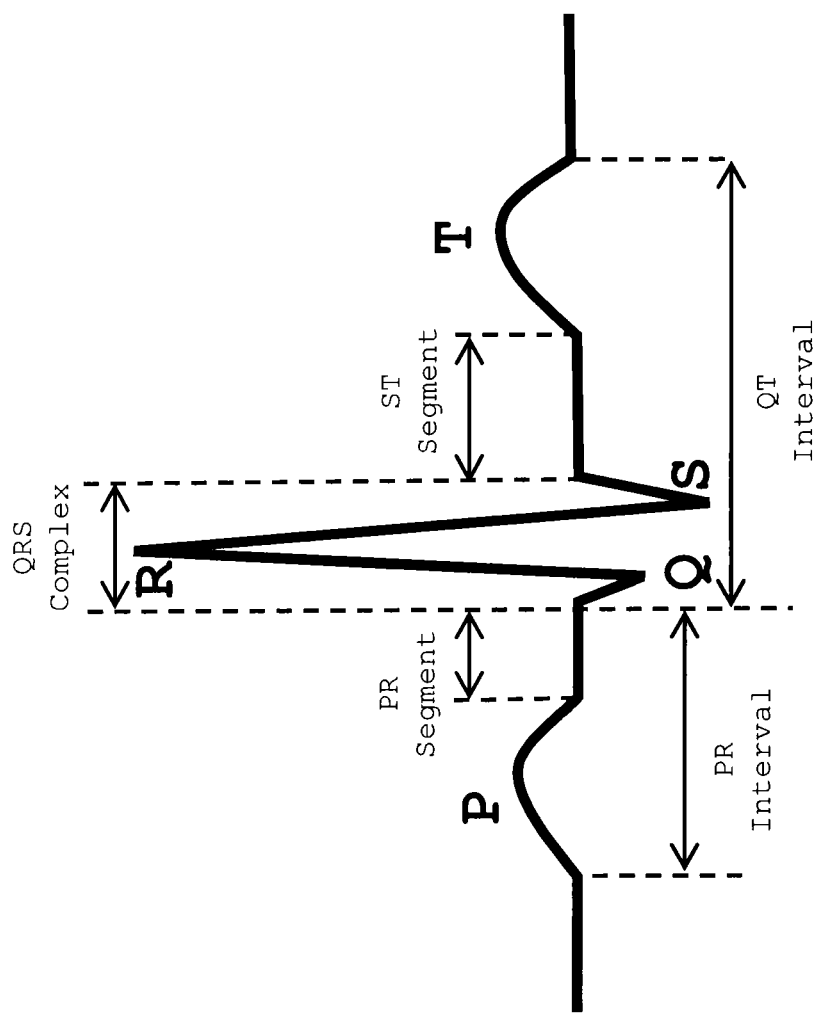
FIG. 5 is an exemplary electrocardiogram signal with related components.

FIG. 5 is an exemplary electrocardiogram signal for a healthy patient. The Electro-Cardiogram (ECG) waveform Electro-Cardiogram is an electric waveform that can be used to monitor the functionality of the heart. The waveform has different segments associated with the functions of the four heart chambers. The P wave is when the blood is pushed from both atria into the ventricles of the heart. The QRS wave is when the blood is pushed out of both ventricles to the body and lugs in ventricular contractions. The T wave is a relaxation of the ventricles and atrial filling. It is noted that physicians observe the ECG waveform and can diagnose the functionality of the heart from reading the different amplitude levels and length of different time segments.

In another embodiment of the present disclosure, a comparator circuit may detect different segments in the ECG waveform. The comparator can detect when the heart starts pumping or receiving blood into or from the circulatory system. It should be noted that the comparator is a circuitry with two inputs. The first input receives a waveform and the second input receives a reference voltage. When the received waveform reaches the reference voltage, the output of the comparators flips. In the present disclosure, the ECG of the patient is used as the input waveform and the reference voltage is the maximum value of the ECG waveform. The pumping of blood into circulatory system (R-wave) can be detected by assigning the reference voltage of the comparator to, for example, 70% of the maximum amplitude in the waveform.

Figure 6:
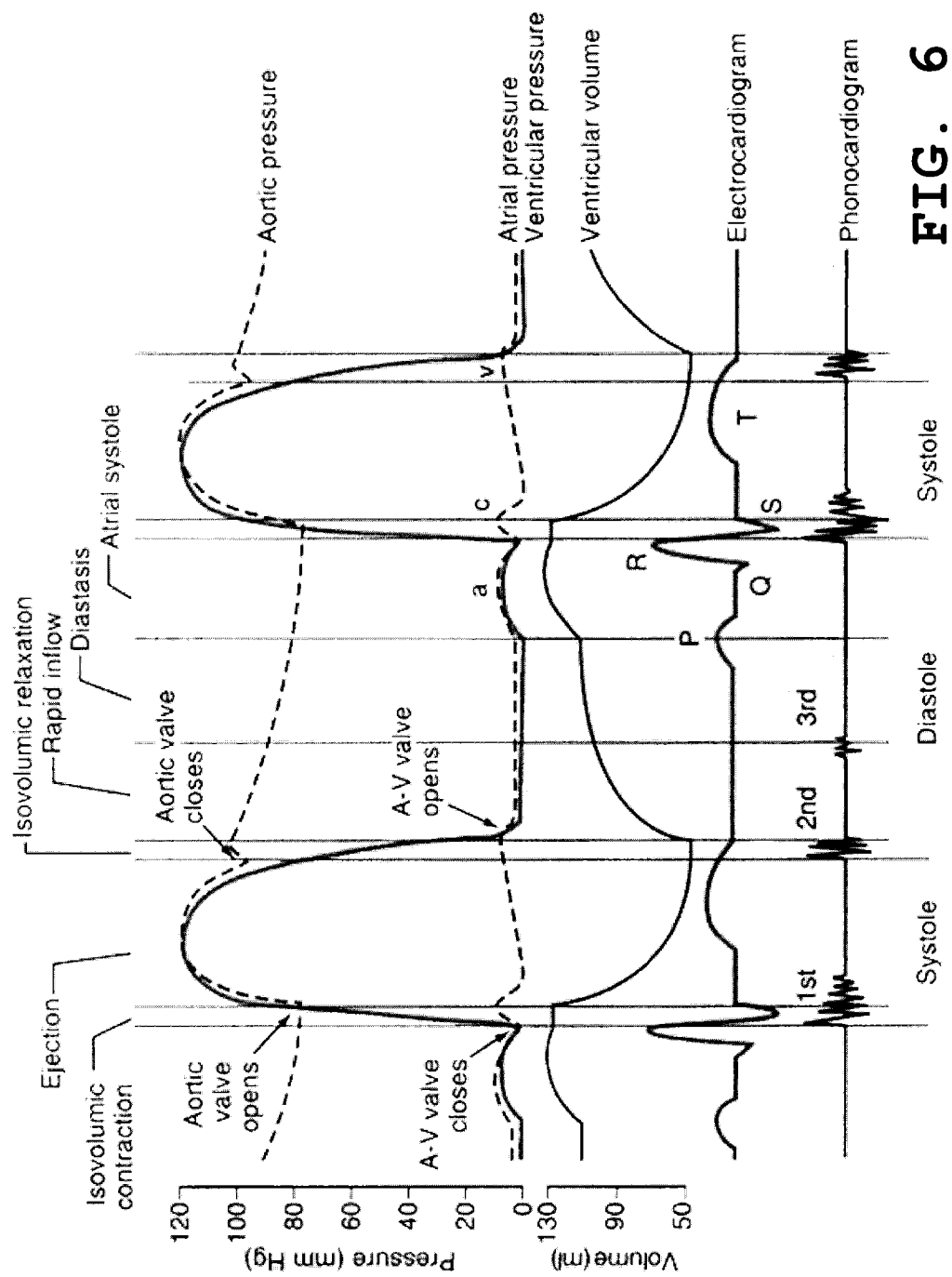
FIG. 6 is an exemplary diagram illustrating cardiac events occurring in the cardiac cycle.
Figure 7:
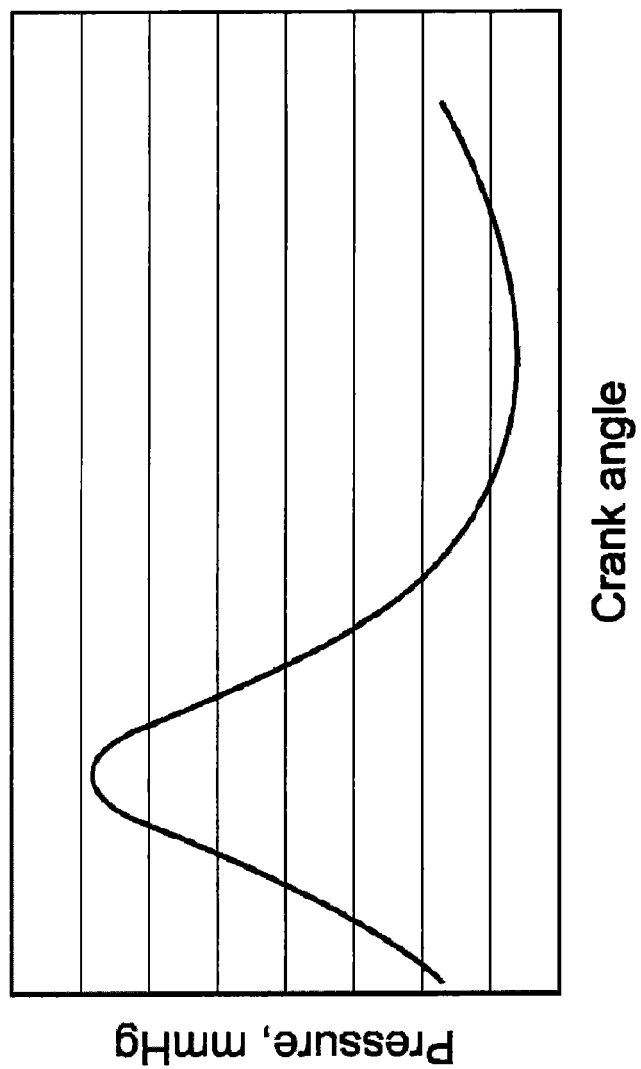
FIGS. 7-10 are exemplary pressure waveforms inside a chamber of a pneumatic circulatory enhancer for diabetic leg therapy.
Figure 8:
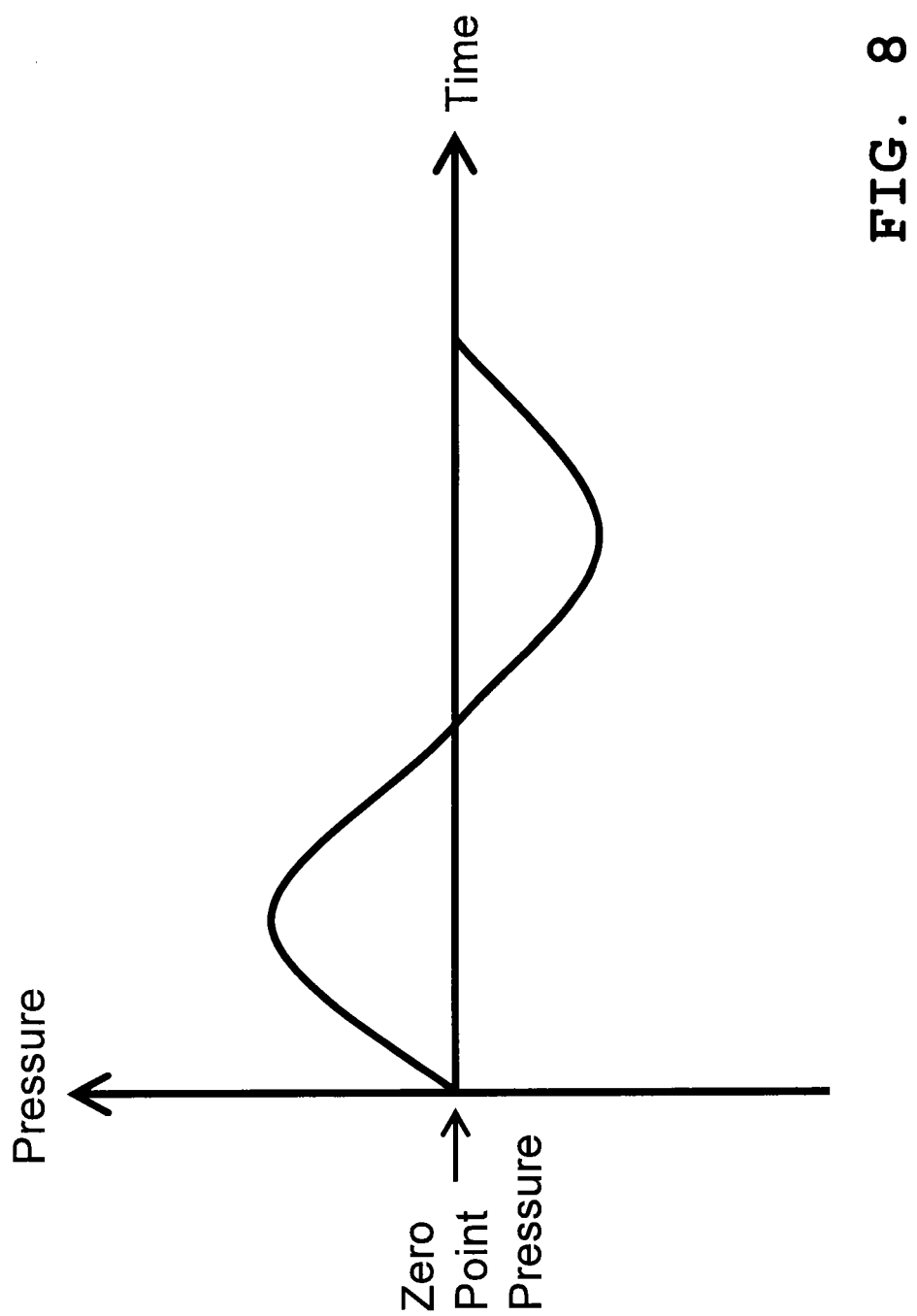
Figure 9:
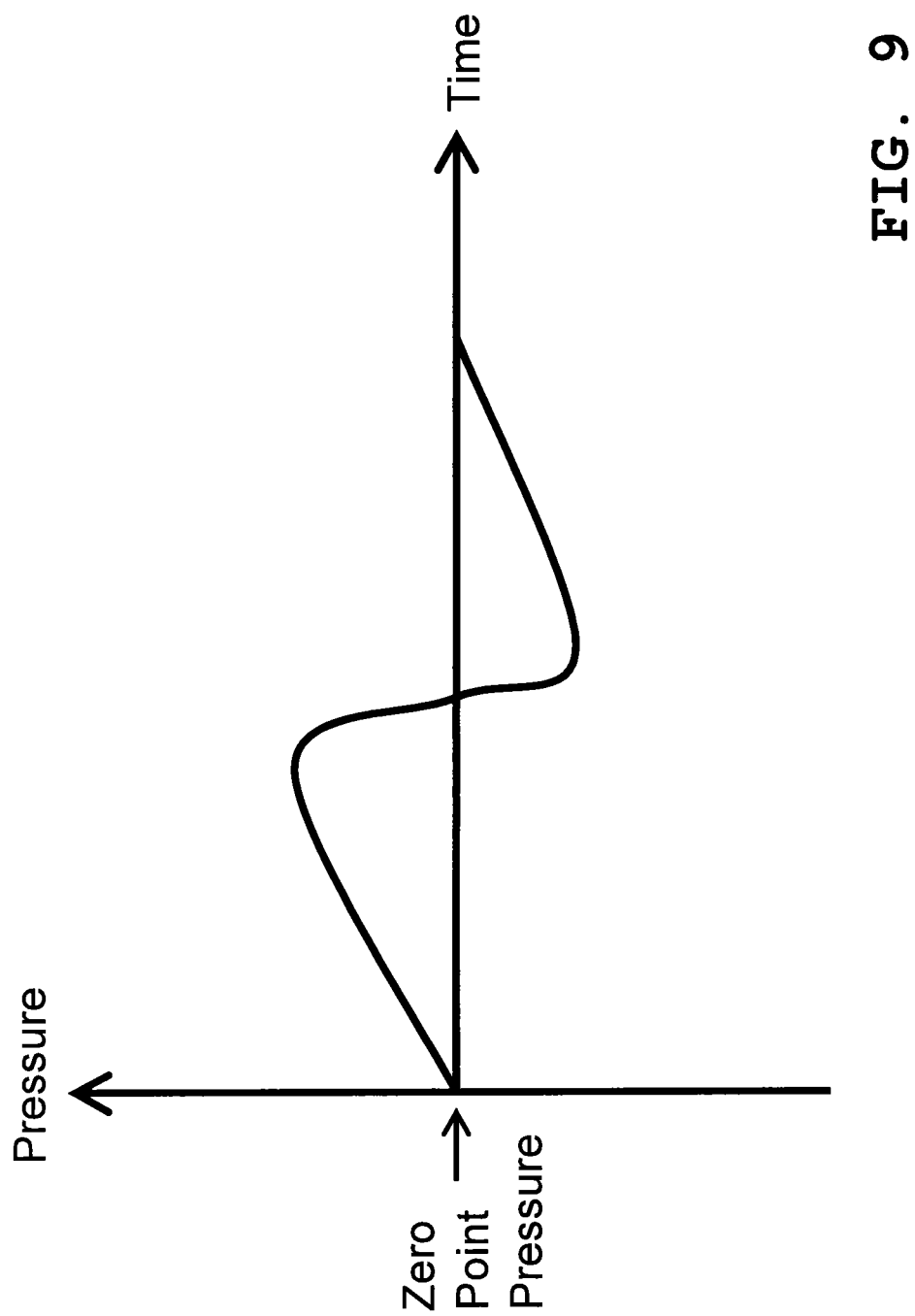
Figure 10:
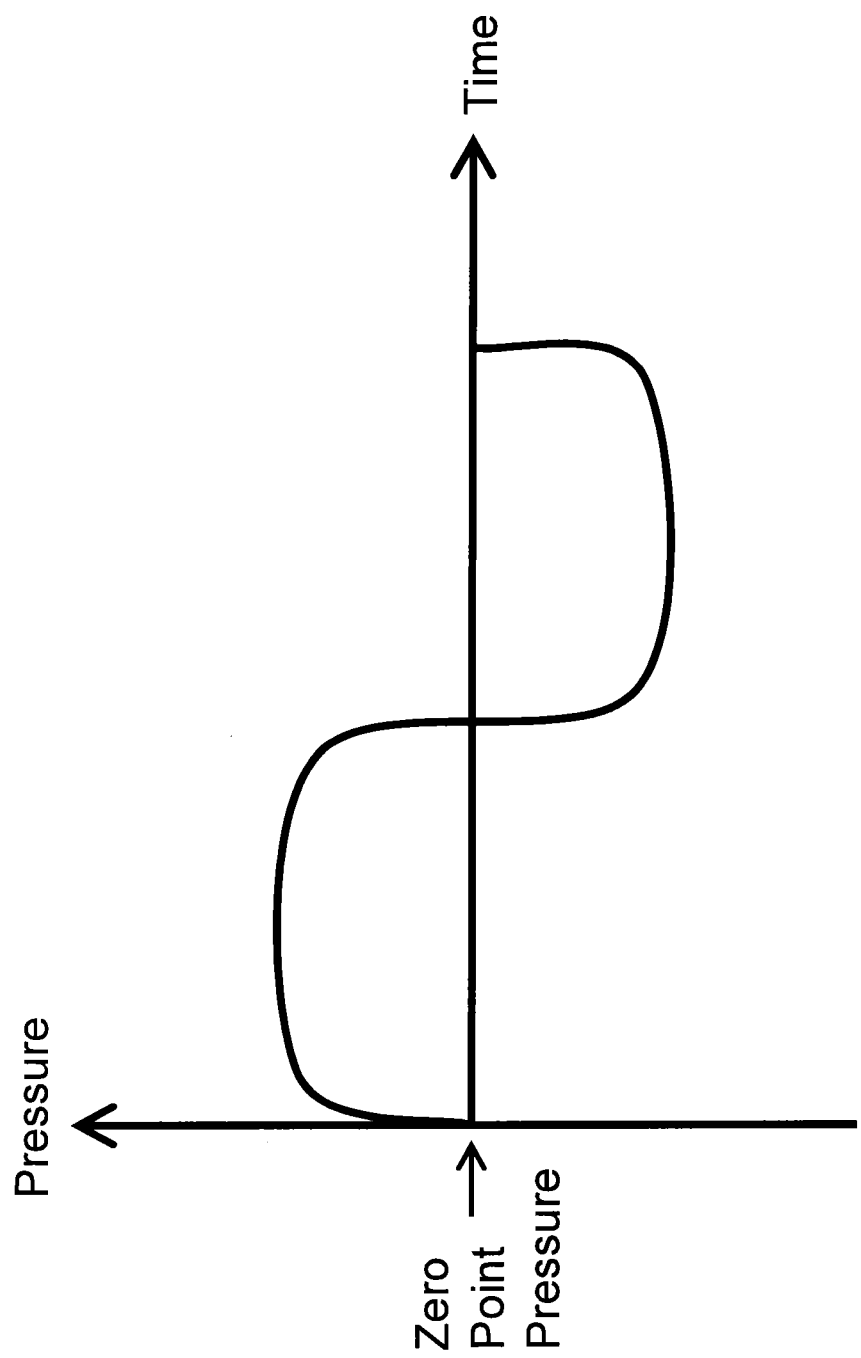

It is noted that the pressure inside the chamber 25 is synchronized with the heartbeats. In an exemplary embodiment, when the left ventricle contracts, the blood is pumped into the body. At this moment, the servo motor 26 drives the pressure inside the chamber 25 around the diabetic leg below the atmospheric pressure to increase the pressure difference between the outer part of the diabetic leg and the left ventricle to attract more blood flow into the leg. The comparator with ECG as the input signal and a threshold of, for example, 70% of maximum ECG signal value can be used to detect the starting of ventricle blood pumping into the body. When the blood returning from the body starts filling the right atrium, the air pump drives the pressure around the diabetic leg 24 higher than the atmospheric pressure (squeeze the leg) to push the blood back to the heart. For example, the air pump drives the pressure around the diabetic leg 24, in the range from 1.01 to 5 times higher than the atmospheric pressure. A second comparator may start to function after the first comparator to detect the QRS complex, which can be used with ECG as the input and reference voltage set to, for example, 20% of maximum ECG signal value to detect the T-wave segment. An exemplary diagram for this operation is shown in FIG. 6. The heart rate may be calculated and used by the controller 20 to control the air pump. FIG. 6 is an exemplary diagram illustrating cardiac events occurring in the cardiac cycle.

The direction of blood flow from the heart can be detected using two ways. The QRS and T complex of the ECG waveform is a preferred technique for determining blood flow and/or synchrony. Another way is by detecting the arterial blood pressure waveform through a pressure sensor or a pulse oximeter and then applying extrema detecting mechanisms to detect the maximum and minimum values for the waveform. The maximum corresponds to blood flowing out of the heart and the minimum corresponds to blood flowing into the heart. Both methods can be used to determine the direction of the blood flow that is needed to synchronize the motor motion.

It is noted that the pneumatic circulatory enhancer 10, as disclosed in this application, improves the blood flow to the affected tissues, is used for the treatment of wounds, and is applicable for intact skin therapy. The pneumatic circulatory enhancer 10, as disclosed in this application, works on intact ischemic or wounded areas of lower limbs.

It is noted that although the present disclosure describes the pneumatic circulatory enhancer with respect to treating a leg, but treating an arm or any other appendage is also in the scope of this application. For example, invention can also be used in a design that fits woman's breasts to enhance the circulation for breast cancer management and cosmetic breast enhancement. In such a configuration the chamber may be designed such that is surrounds a breast and/or the upper body portion of a patient. When used in a configuration that fits a human breast the pneumatic circulatory enhancer may function to improve circulation in the breast. Improved circulation may consequently provide improved delivery of chemotherapeutic agents to affected tissues. This in turn may permit the use of a relatively lower dose of chemotherapeutic agent.

When used in a configuration for cosmetic enhancement of breast size and/or shape the pneumatic circulatory enhancer may act to train, support or direct soft tissue to provide a cosmetically desirable result. The pneumatic circulatory enhancer may be used on a periodic basis for purely cosmetic purposes and/or may be used in conjunction with breast reconstruction or enhancement surgery to encourage tissue growth and/or tissue mending and orientation.

In a further embodiment of the invention the chamber may be configured to fit the scalp to enhance the circulation. Such a configuration may function to improve circulation in the scalp dermal and sub-dermal tissues to stimulate air growth and/or reverse hair loss or balding.

The foregoing discussion discloses and describes merely exemplary embodiments. As will be understood by those skilled in the art, the present application may be embodied in other specific forms without departing from the spirit or essential characteristics thereof. Accordingly, the present disclosure is intended to be illustrative, but not limiting of the scope of the application, as well as other claims. The disclosure, including any readily discernible variants of the teachings herein, defines, in part, the scope of the foregoing claim terminology such that no inventive subject matter is dedicated to the public.

The invention claimed is:

1. A pneumatic circulatory enhancer to enhance a blood flow of a leg of a patient, the pneumatic circulatory enhancer comprising:
    a chamber adapted to surround the leg and is filled with gas having a negative pressure, a zero-point pressure, or a positive pressure;
    a pneumatic gas pump having a cylinder and a piston that is connected to the chamber via a tube, the piston moving in the cylinder by an electrical motor;
    a plurality of ECG electrodes that are adapted to be connected to body parts of the patient and detect ECG signals, which are indicators of heartbeats of the patient, from the patient;
    a pressure sensor that is connected to the chamber and measures a pressure of the gas inside the chamber;
    a controller that receives the ECG signals from the plurality of ECG electrodes and controls the electrical motor based on the received ECG signals to pump-in/ pump-out the gas to/from the chamber by moving the piston inside the cylinder, wherein the zero-point pressure is an atmospheric pressure that the pneumatic circulatory enhancer is operated, the negative pressure is any pressure smaller than the zero-point pressure, and the positive pressure is any pressure greater than the zero-point pressure.

2. The pneumatic circulatory enhancer according to claim 1, wherein the controller via the pneumatic gas pump increases or decreases the pressure of the gas inside the chamber in-synchrony with the heartbeats of the patient.

3. The pneumatic circulatory enhancer according to claim 2, wherein upon determination by the controller, based on the received ECG signals, the patient's heart is pumping the blood into the leg, the controller moves the piston to generate the negative pressure inside the chamber, and upon determination by the controller, based on the received ECG signals, that the heart of the patient is pumping the blood out of the leg, the controller moves the piston to generate the positive pressure inside the chamber.

4. The pneumatic circulatory enhancer according to claim 2, wherein upon determination of a QRS-wave by the controller, based on the received ECG signals, the electrical motor moves the piston to decrease the pressure of the gas inside the chamber, and upon determination of a T-wave by the controller, based on the received ECG signals, the electrical motor moves the piston to increase the pressure of the gas inside the chamber.

5. The pneumatic circulatory enhancer according to claim 4, further comprising:

a sealer that is positioned between the chamber and the leg in an opening of the chamber and seals the opening of the chamber to prevent air leak from the chamber; and a ventilation valve that is connected to the chamber and is controlled by the controller.

6. The pneumatic circulatory enhancer according to claim 1, further comprising:

an oxygen tank connected to the chamber via an oxygen valve, the oxygen valve being controlled by the controller, to supply oxygen to the chamber when the valve is open; and an oxygen sensor connected to the chamber that measures a concentration of the oxygen gas inside the chamber and transmits measured oxygen concentration to the controller.

7. The pneumatic circulatory enhancer according to claim 1, wherein the chamber has a first part and a second part such that the first part and the second part rotate around a plurality of hinges, and the leg is positioned in the first part, and the second part is rotated around the hinges to surround the leg between the first part and the second part.

8. The pneumatic circulatory enhancer according to claim 1, wherein the pressure of the gas inside the chamber corresponds to a wave form of the ECG signals.

9. A method for enhancing blood flow in a leg of a patient, the method comprising the steps of:

placing the leg inside a chamber and sealing an opening of the chamber to prevent air leak from the chamber;

monitoring the patient's heartbeats via a plurality of ECG electrodes that are adapted to be connected to the patient;

detecting, by a controller, a wave shape of ECG signals received from the ECG electrodes connected to the patient;

monitoring an air pressure inside the chamber; and adjusting the air pressure inside the chamber based on the wave shape of the ECG signals, wherein when the controller detects, based on the received wave shape of ECG signals, that the patient's heart is pumping the blood into the leg, the controller decreases the air pressure of the chamber via a pneumatic gas pump, and when the controller detects, based on the received wave shape of ECG signals, that the patient's heart is pumping the blood out of the leg, the controller increases the air pressure of the chamber via the pneumatic gas pump.

10. The method for enhancing blood flow in a leg of a patient according to claim 9, wherein the air pressure of the chamber is decreased to increase the delivery of the blood from the heart to the leg, and the air pressure of the chamber is increased to the push the blood from the leg back to the heart.

11. The method for enhancing blood flow in a leg of a patient according to claim 9, wherein the air pressure inside the chamber is adjusted in-synchrony with the heartbeats of the patient.

12. The method for enhancing blood flow in a leg of a patient according to claim 11, further comprising the steps of:

decreasing the air pressure inside the chamber when a QRS-wave is detected in the received ECG signals; and increasing the air pressure inside the chamber when a T-wave is detected in the received ECG signals.

13. The method for enhancing blood flow in a leg of a patient according to claim 11, further comprising the steps of:

opening a ventilation valve for pumping out the air in chamber:

opening an oxygen valve for filling the chamber with oxygen gas from an oxygen tank;

monitoring a concentration of the oxygen gas inside the chamber; and closing the oxygen valve and the ventilation valve when the concentration of the oxygen gas inside the chamber is above a predetermined threshold.

14. The method for enhancing blood flow in a leg of a patient according to claim 13, further comprising the steps of:

measuring the air pressure inside the chamber after the step of adjusting;

determining whether or not the measured air pressure inside the chamber is outside of a predetermined pressure range;

adjusting the air pressure inside the chamber to zero-point pressure and obtaining a next ECG signal from the patient when the measured air pressure is outside the predetermined pressure range; and obtaining a next ECG signal from the patient when the measured air pressure is within the predetermined range.

15. A non-transitory computer readable medium including executable instructions, which when executed by a controller, cause a processor to execute a method for enhancing blood flow in a leg of a patient, the method comprising:

monitoring the patient's heartbeats via a plurality of ECG electrodes that are adapted to be connected to the patient;

detecting a wave shape of ECG signals received from the ECG electrodes adapted to be connected to the patient;

monitoring the air pressure inside a chamber surrounding the leg of the patient via a pressure sensor connected to the chamber; and adjusting the air pressure inside the chamber based on the wave shape of the ECG signals by moving a piston of an air pump connected to the chamber with an electrical motor, wherein when the controller detects, based on the received wave shape of ECG signals, that the patient's heart is pumping the blood into the leg, the controller decreases the air pressure of the chamber via a pneumatic gas pump, and when the controller detects, based on the received wave shape of ECG signals, that the heart of the patient is pumping the blood out of the leg, the controller increases the air pressure of the chamber via the pneumatic gas pump.

16. The non-transitory computer readable medium according to claim 15, the method further comprising:

decreasing the air pressure of the gas inside the chamber when a QRS-wave is detected; and increasing the air pressure of the gas inside the chamber when a T-wave is detected.

17. The non-transitory computer readable medium according to claim 16, the method further comprising:

opening a ventilation valve for pumping out the air in chamber;

opening an oxygen valve for filling the chamber with oxygen gas from an oxygen tank;

monitoring a concentration of the oxygen gas inside the chamber; and closing the oxygen valve and the ventilation valve when the concentration of the oxygen gas inside the chamber is above a predetermined threshold.

18. The non-transitory computer readable medium according to claim 17, the method further comprising:

measuring the air pressure inside the chamber after the step of adjusting;

determining if the measured air pressure inside the chamber is outside of a predetermined pressure range;

adjusting the air pressure when the measured air pressure is outside the predetermined pressure range; and obtaining a next ECG signal from the patient when the measured air pressure is within the predetermined range.

* * * * *